United States Patent [19]

Sih

[11] 4,336,371
[45] Jun. 22, 1982

[54] 2-DECARBOXY-2-TETRAZOLYL-13,14-DIHYDRO-PG$_2$ COMPOUNDS

[75] Inventor: John C. Sih, Kalamazoo, Mich.

[73] Assignee: The Upjohn Company, Kalamazoo, Mich.

[21] Appl. No.: 85,616

[22] Filed: Oct. 17, 1979

Related U.S. Application Data

[62] Division of Ser. No. 26,066, Apr. 2, 1979, Pat. No. 4,243,611.

[51] Int. Cl.$^3$ ............... C07D 257/06; C07D 409/08; A61K 31/41

[52] U.S. Cl. ................... 542/429; 548/253; 484/269

[58] Field of Search ............ 542/429; 548/253

[56] References Cited

U.S. PATENT DOCUMENTS 3,932,389 1/1976 Johnson et al. ............ 542/252
4,064,351 12/1977 Sakai et al. ............ 542/426

*Primary Examiner*—David B. Springer
*Attorney, Agent, or Firm*—Lawrence T. Welch; Robert A. Armitage

[57] ABSTRACT

The present invention provides novel 2-decarboxy-2-tetrazolyl-13,14-dihydro-PG$_2$ compounds methods for their preparation and pharmacological use for the induction of prostaglandin-like effect.

1 Claim, No Drawings

2-DECARBOXY-2-TETRAZOLYL-13,14-DIHYDRO-PG$_2$ COMPOUNDS

CROSS REFERENCE TO RELATED APPLICATIONS

The present application is a division of Ser. No. 026,066, filed Apr. 2, 1979, now U.S. Pat. No. 4,243,611 issued Jan. 6, 1981.

BACKGROUND OF THE INVENTION

The present invention relates to novel prostaglandin analogs. Particularly, these compounds are analogs of the prostaglandins wherein the C-20-C-19 position is unsaturated, i.e., 19,20-didehydro-PG compounds. Most particularly, the present invention relates to novel 2-decarboxy-2-tetrazolyl-13,14-dihydro-PG$_2$ compounds, a disclosure of the preparation and use of which is incorporated here by reference from U.S. Ser. No. 025,899, filed Apr. 2, 1979, now 4,228,104, issued Oct. 14, 1980.

PRIOR ART

Prostaglandin analogs exhibiting unsaturation in the C-17, C-18, or C-20 position are known in the art. See, for example, U.S. Pat. No. 3,919,285 German Offenlegungsschrift 2,635,985 (and its corresponding Derwent Farmdoc CPI No. 10302A), and U.S. Pat. No. 4,064,351 for examples of such compounds. See also the reference cited in U.S. Ser. No. 026,066.

SUMMARY OF THE INVENTION

The present invention particularly provides: A compound of the formula

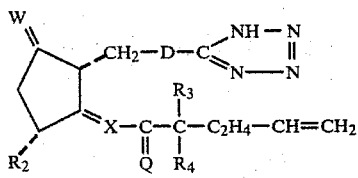

where D is
(1) cis—CH=CH—CH$_2$—(CH$_2$)$_g$—CH$_2$—,
(2) cis—CH=CH—CH$_2$—(CH$_2$)$_g$—CF$_2$—,
(3) cis—CH$_2$—CH=CH—CH$_2$—C$_2$—,
(4) trans-(CH$_2$)$_3$—CH=CH—,
wherein Q is

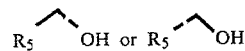

wherein R$_5$ is hydrogen or methyl,
wherein R$_2$ is hydrogen, hydroxyl, or hydroxymethyl;
wherein R$_3$ and R$_4$ are hydrogen, methyl, or fluoro, being the same or different, with the proviso that one of R$_3$ and R$_4$ is fluoro only when the other is hydrogen or fluoro;
wherein W is

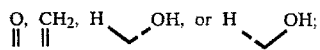

and wherein X is —CH$_2$CH$_2$—.

The compounds of the present invention are particularly useful for inducing prostaglandin-like biological effects, as is described in U.S. Ser. No. 026,066. Uses of compounds in accordance with the present invention include, therefore, anti-asthmatic indication.

I claim:
1. A compound of the formula

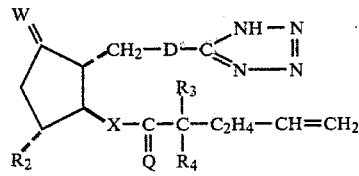

wherein D is
(1) cis—CH=CH—CH$_2$—(CH$_2$)$_g$—CH$_2$—,
(2) cis—CH=CH—CH$_2$—(CH$_2$)$_g$—CF$_2$—,
(3) cis—CH$_2$—CH=CH—CH$_2$—CH$_2$—,
(4) trans—(CH$_2$)$_3$—CH=CH—,
wherein g is zero, one, 2, or 3,
wherein Q is

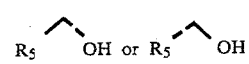

wherein R$_5$ is hydrogen or methyl,
wherein R$_2$ is hydrogen, hydroxyl, or hydroxymethyl;
wherein R$_3$ and R$_4$ are hydrogen, methyl, or fluoro, being the same or different, with the proviso that one of R$_3$ and R$_4$ is fluoro only when the other is hydrogen or fluoro;
wherein W is

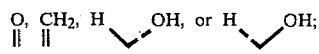

and wherein X is —CH$_2$CH$_2$—.

* * * * *

UNITED STATES PATENT OFFICE
CERTIFICATE OF CORRECTION

Patent No. 4,336,371         Dated   June 22, 1982

Inventor(s)   John C. Sih

It is certified that error appears in the above-identified patent and that said Letters Patent are hereby corrected as shown below:

Column 1, line 56, "(3) cis-$CH_2$-CH=CH-$CH_2$-$C_2$-," should read -- (3) cis-$CH_2$-CH=CH-$CH_2$-$CH_2$-, --.

Signed and Sealed this

Fourth Day of January 1983

[SEAL]

Attest:

Attesting Officer

GERALD J. MOSSINGHOFF

Commissioner of Patents and Trademarks